United States Patent [19]
King et al.

[11] Patent Number: 5,395,356
[45] Date of Patent: Mar. 7, 1995

[54] CORRECTION OF PRESBYOPIA BY PHOTOREFRACTIVE KERATECTOMY

[75] Inventors: Michael C. King, Carlisle; Peter J. Klopotek, Framingham, both of Mass.

[73] Assignee: Summit Technology, Inc., Waltham, Mass.

[21] Appl. No.: 72,529

[22] Filed: Jun. 4, 1993

[51] Int. Cl.⁶ .................... A61N 5/06; A61B 17/00
[52] U.S. Cl. .............................. 606/4; 606/11; 606/5; 606/12
[58] Field of Search ............ 606/6, 5, 4, 10, 11, 606/12

[56] References Cited

U.S. PATENT DOCUMENTS

| | | | |
|---|---|---|---|
| 4,838,266 | 6/1989 | Koziol et al. | 606/4 |
| 4,941,093 | 7/1990 | Marshall et al. | 606/5 |
| 4,973,330 | 11/1990 | Azema et al. | 606/5 |
| 5,019,074 | 5/1991 | Muller | 606/5 |

FOREIGN PATENT DOCUMENTS

0412789  2/1991  European Pat. Off. ........... 606/5

*Primary Examiner*—David M. Shay
*Assistant Examiner*—Sonya C. Harris
*Attorney, Agent, or Firm*—Thomas J. Engellenner; Ann Lamport Hammitte

[57] ABSTRACT

Methods and apparatus are disclosed for the correction of presbyopia by reprofiling the cornea to create at least one region having a different focal point, and thereby assist the eye in accommodating for close-viewing conditions. According to the invention, at least one region of different curvature is created by photoablation of the cornea to permit the eye to accommodate for near objects. This "add" region is preferably located near the center of the optical zone and preferably within Bowman's membrane or the adjacent upper portions of the stroma, which lies directly below Bowman's membrane. Apparatus is disclosed, including a laser means and a beam-shaping means, disposed between the laser means and the surface of the cornea, which imposes a defined ablation profile upon the cornea. The system can also include a feedback control means for measuring the effectiveness of the laser during operation and for controlling the laser. The beam-shaping means can include either an aperture e.g., a beam-shaping stop means alone or in combination with a beam-shaping window, or an mask which is photodecomposable or otherwise graded in its absorptive capacity to present a predefined profile of resistance to the laser radiation.

10 Claims, 6 Drawing Sheets

CORRECTION OF PRESBYOPIA BY PHOTOREFRACTIVE KERATECTOMY

BACKGROUND OF THE INVENTION

The technical field of this invention is corneal surgery and, in particular, the invention relates to systems and methods of compensating for presbyopia by reprofiling the cornea of the eye.

As individuals age, the human eye loses its ability to focus on nearby objects. Between the fourth and fifth decades of life, the condition often becomes so pronounced that simple tasks, such as reading are difficult. This condition, known as presbyopia, is due to a progressive loss in the elasticity of the lens of the eye, such that the ciliary muscles which normally force the lens in a rounded shape to accommodate near objects can no longer exert the necessary changes in the lens' shape.

The conventional optometric solution to the problem of presbyopia is a prescription of reading glasses or, for individuals who already require glasses to correct other refractive errors such as myopia or astigmatism, a prescription of bifocal or multifocal glasses.

Recently, it has been demonstrated that changes in the refractive power of the eye can be achieved by laser ablation of the corneal surface. Such procedures, known as photorefractive keratectomy (PRK), involves the use of a nonthermal, high energy, pulsed laser to effectively sculpt the cornea into an ideal shape. For details, see, Marshall et al. "Photablative Reprofiling of the Cornea using an Excimer Laser: Photorefractive Keratectomy," Vol. 1, *Lasers in Ophthalmology*, pp. 21–48 (1986); and Tuft et al. "Stromal Remodelling Following Photorefractive Keratectomy," Vol. 1, *Lasers in Ophthalmology*, pp. 177–183 (1987), herein incorporated by reference.

The cornea of the eye is composed of a set of distinct layers: the outer epithelium, an anterior elastic lamina known as "Bowman's membrane," the cornea proper (or "stroma"), a posterior elastic lamina known as "Descemet's membrane", and the inner endothelium. The stroma is fibrous and transparent and constitutes the major portion of the cornea. Bowman's membrane, which forms the outer elastic lamina, is a rigid fibrillar structure not tending to cut or fracture, while Descemet's membrane, which forms the inner elastic lamina, is very brittle but elastic and has a tendency to curl. Together, the Bowman's and Descemet's membranes impart the necessary curvature to the stromal tissue.

Photorefractive keratectomy involves the use of a laser photoablation apparatus in which the size of the exposed area on the surface of the cornea is varied to control the reprofiling operation. In one embodiment, a beam-shaping stop or window is moved axially along the beam to increase or decrease the region of cornea on which the laser radiation is incident. By progressively varying the size of the exposed region, a desired photoablation profile is established on the surface. For further details on this technique, see U.S. Pat. No. 4,941,093 issued to Marshall et al. on Jul. 10, 1990, herein incorporated by reference.

Another new technique for corneal reshaping involves the use of a laser photoablation apparatus in which a beam-shaping mask is disposed between the laser and the surface. In one embodiment, the mask provides a predefined profile of resistance to erosion by laser radiation whereby a portion of the laser radiation is selectively absorbed and another portion is transmitted to the surface in accordance with the mask profile. For further disclosure of such masking techniques, see U.S. Pat. No. 4,856,513 issued to Muller on Aug. 15, 1989; U.S. Pat. No. 4,994,058 issued to Raven et al. on Feb. 19, 1991; and U.S. Pat. No. 5,019,074 issued to Muller on May 28, 1991, also incorporated herein by reference.

It is an object of the present invention to provide methods whereby laser surgical techniques can be applied to the eye to provide a correction for presbyopia.

SUMMARY OF THE INVENTION

Methods and apparatus are disclosed for the correction of presbyopia by reprofiling the cornea to create at least one region having a different focal point to assist the eye in accommodating for close-viewing conditions.

According to the invention, at least one region of different curvature is created by photoablation of the cornea to permit the eye to accommodate for near objects. This "add" region is preferably located near the center of the optical zone and preferably within Bowman's membrane or the adjacent upper portions of the stroma, which lies directly below Bowman's membrane.

The system comprises a laser means capable of generating ablative laser radiation and a beam-shaping means, disposed between the laser means and the surface of the cornea, which imposes a defined ablation profile upon the cornea to provide at least one region having a different refractive surface. The system can also include a feedback control means for measuring the effectiveness of the laser during operation and for controlling the laser, such that the reprofiling operation is substantially confined to the Bowman's membrane throughout the procedure.

According to another aspect of the invention, there is o provided a method of repro filing the surface of the cornea to provide a multifocal capability to the eye by photoablation of one or more selective regions of the cornea. This is accomplished by disposing a beam-shaping means between a source of ablative radiation and the cornea to vary the beam dimensions and thereby provide selective removal of portions of the Bowman's membrane or, if necessary, the corneal stroma.

In this method, the exposure area on the surface of the cornea to which the pulses are delivered is adjusted in a controlled manner thereby to create at least one "add" region to assist the eye in accommodating for close viewing of objects. The beam-shaping means described herein may comprise either an aperture, e.g., a beam-shaping stop means alone or in combination with a beam-shaping window, or a mask which is photodecomposable or otherwise graded in its absorptive capacity to present a predefined profile of resistance to the laser radiation.

The methods of the present invention can also include measuring the changes in the curvature of the cornea and comparing such measurements with desired values for both the overall corneal curvature and the curvature of the add region to provide feedback control signals for the laser means and/or beam-shaping means.

The invention, thus, provides a method and apparatus for repro filing the surface of the cornea for correcting general refractive errors in the eye (e.g., myopia, hyperopia and astigmatism) and also for adding at least one region that has a different focal point, by employing an ablative laser source and a beam delivery system to repro file the cornea and form an aspherical curvature in the surface of the eye.

As noted above, the systems and methods of the present invention are particularly well-suited for controlled reprofiling of the cornea, particularly the collagen sublayer known as Bowman's membrane, which lies immediately below the uniform, extremely thin, epithelial layer of the cornea. Although the Bowman's membrane and the stroma together form the collagen components of the cornea, Bowman's membrane is a rigid fibrillar sublayer, which can be ablated with precision by excimer radiation. It has been discovered by the present inventors that significant changes in the refractive power of the eye (including the formation of an add region) can be achieved by the ablation of a controlled volume of corneal tissue, largely confined to Bowman's membrane (typically from about 5 to 40 micrometers thick), and that such changes in shape remain constant with narrow limits even after healing of the ablated membrane region.

Alternatively, the ablative process can be performed with penetration into the stromal region of the cornea underlying Bowman's membrane, particularly when it is desirable to effect a change in curvature or create an aspherical zone over a wider portion of the optical zone (e.g., reprofiling operations that extend over about 5 millimeters or more of corneal surface). Changes in the shape of the stromal region, likewise, remain constant. However, care must be exercised in performing deeper ablations because the overall thickness of the typical cornea extends only about 400 to about 500 micrometers in depth and the integrity of Descemet's membrane and the endothelial lining at the posterior surface of the cornea must not be compromised.

In the practice of the present invention, the epithelial layer can be very rapidly ablated on exposure to the laser light. The extremely thin surface layer heals and eventually reforms following the reshaping operation. In surgical applications, the ablative laser light can be of a wavelength obtainable, for example, from a UV argon fluoride laser, typically about 193 nanometers, which does not penetrate through the cornea.

According to a preferred feature of the invention, the laser wavelength and power are selected so that the laser energy incident on the surface layers of the cornea is absorbed by the epithelium and Bowman's layer so that there is little or no energy remaining to penetrate into, or otherwise affect, the stroma or underlying structures of the eye.

Preferably, the laser is pulsed repeatedly and, using an iris, diaphragm, optical stops, mirrors, beamsplitters, masks or other similar devices, the pulses of energy are directed towards the corneal surface either in their entirety or partially, and/or towards a selected region or selected regions of the surface, so that, over a period of time, different regions of the surface are exposed to different quantities of energy from the laser source, so as to produce differential ablation of the surface. In the present invention, the net effect is to create at least one region having a different focal point to assist the eye in accommodating for close-viewing conditions.

Typically, this "add" zone will require an increase in the convexity of the corneal surface. This can be achieved by exposing the surface of the add zone to a succession of pulses of light energy while controlling the area exposed by each pulse, such that the central region of the add zone will be exposed to less energy than the peripheral regions, so that lesser erosion occurs in the central region relative to the peripheral regions of the zone and thereby increase the convexity of the corneal surface in the add zone.

The present invention can also be practiced in conjunction with general photorefractive keratectomy (PRK) to provide both an overall repro filing of the corneal surface and also one or more discrete add zones. In general, myopic conditions can be corrected by imparting a flatten curvature to the cornea overall. This can be achieved by exposing the optical zone generally (i.e., the central region of the cornea, approximately 2 millimeters to about 7 millimeters in diameter) to a succession of pulses of light energy while controlling the area exposed by each pulse, so as to successively reduce the exposure area. In this way, the central region of the cornea will be exposed to more energy than the peripheral regions, so that greater erosion occurs in the central region relative to the peripheral regions of the zone and thereby reduce the convexity of the overall corneal surface. Conversely, if an increase in convexity is required (e.g., to correct hyperopia), the opposite approach is used, and the peripheral regions are exposed to a greater extent than the central region, thereby leaving a "hill" in the middle of the Bowman's membrane by selective application of laser energy. In the practice of the present invention, hyperopia would be corrected by repro filing the cornea to provide normal visual acuity over most of the optical zone, but one portion of the new surface would be further raised with a different focal point to provide the add zone.

Similar composite profiles can be achieved for correction of astigmatism and presbyopia. To achieve a correction of astigmatism, the ablative radiation is selectively applied to the eye, in accordance with the astigmatic axis to preferentially flatten the curvature along the axis where the astigmatic bulge is present. Again, in conjunction with correction of astigmatism, an add zone is created in one portion of the optical region.

The overall repro filing operations and the provision of the add zone can be performed sequentially or simultaneously. In one approach, the beam shaping means of the present invention can provide a first series or sequence of apertures that perform a general reprofiling operation and a second set or series of apertures then used to create the add zone. Alternatively, the beam shaping means can include an erodable or otherwise graded mask which transfers a composite profile to the cornea in one step. (It should be appreciated that the methods of the present invention can also be used to create more than one discrete add zone, as well as multifocal or aspheric surfaces in which the curvature is continuously varied.)

In a preferred arrangement of the invention, a measuring device is included within the apparatus for measuring a parameter which is a function of the corneal surface, such as refractive power or surface curvature. The measuring device can further include input means, such as a keyboard and/or a random access memory device, for receiving an input defining a desired value for the parameter, comparison means for o comparing the measured value of the parameter with the desired value, and control signal generating circuit means for generating control signals for the laser from the comparison, the control signals serving inter alia, to determine the area over which the laser pulses are effective, thereby to obtain the desired shape to the corneal surface and, preferably, to insure that the surface of the cornea is repro filed with minimal disturbance of the stroma.

In one embodiment, the comparison means and the control means are provided by a computer system incorporating the random access memory. The input may specify the desired corneal curvature directly, or it may define it by specifying a desired value for another related parameter from which the desired erosion profile for provision of an add zone (as well as other PRK procedures) can be derived.

The laser light source preferably is designed so as to produce pulses of light having substantially constant energy density, such that a known depth of surface material will be eroded for each pulse. By using relatively low power, only a microscopically thin layer of material will be removed in response to each pulse. By continual monitoring and feedback, a very accurate profiling of the cornea can be achieved.

An automatic feedback control system may be provided in which the output from a measuring device for measuring the shape or an optical property of the eye is used to control the delivery of pulses of laser energy. Alternatively, the desired surface profile may be obtained through erosion by a successive approximation technique. In this technique, a measuring device is used to determine the change it is desired to make in the profile of the surface. Pulses of laser energy are delivered to the surface so as to bring about slightly less than the desired alteration. The measuring device is used again to determine the correction now needed to reach the desired profile, and further pulses of laser energy are provided accordingly to produce slightly less than the total calculated correction. This process is repeated until the eroded surface acquires the desired profile to a suitable degree of accuracy.

Suitable measurement devices, commonly called keratometers, are known and commercially available. Examples of such devices include the "Photokeratoscope" manufactured by the Sun Contact Lens Company of Kyoto, Japan, and the "Corneascope" manufactured by International Diagnostic Instruments Limited, Broken Arrow, Okla., USA. (See also, Klyce, "Computer Assisted Corneal Topography," Vol. 25, *Invest. Ophthalmol. Vis. Sci.*, p. 1435 (1984) for a comparison of these instruments and a method of using the "Photokeratoscope").

In order to locate the eye relative to the laser means, conventional suction rings or cups may be used, such as those provided by Steinway Instruments of San Diego, Calif., USA. Alternatively, modified vacuum-fixed stages supporting erodable masks, as described in more detail below, can be used. In either event, the fixation means is typically applied to the white (sclera) region of the eye and connected to a low suction pressure sufficient to clamp the cup or stage to the eye but not so great that the cornea is distorted. The cup or stage may then be fixed to further apparatus (in the present case, this will normally be the optical system of the laser) which will thereby be located accurately with respect to the eye. The use of such devices to immobilize an eye is shown on page 39 of *Ophthalmology Times* of Jul. 1, 1986, and such a procedure is well-known in the art.

Excimer lasers and halogen lasers operating to generate UV radiation are presently preferred for corneal ablation and, in particular, argon-fluoride (ArF) excimer lasers operation at about 193 nm are preferred. In medical uses such as corneal ablation, it is preferred to use an excimer laser which is designed for medical applications, such as the EXCIMED and OMNIMED systems manufactured by Summit Technology, Inc. of Waltham, Mass., USA.

The pulse repetition rate for the laser may be chosen to meet the needs of each particular application. Normally the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser and the nature of the irradiated object. For any given wavelength of laser energy applied to any given material, there typically will be a threshold value of energy density below which significant erosion does not occur. Above the threshold density, there will be a range of energy densities over which increasing energy densities give increasing depths of erosion, until a saturation value is reached. For increases in energy density above the saturation value, no significant increase in erosion occurs.

The threshold value and the saturation value can vary from wavelength to wavelength of laser energy and from one layer of the cornea to another layer. However, for any particular laser and any particular material, the values can be found readily by experiment.

For example, in the case of eroding Bowman's membrane portion of the cornea by energy of wavelength 193 nm (the wavelength obtained from an ArF Excimer laser), the threshold value is about 50 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from an $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the cornea pulses of an energy density of 90 to 220 mJ per $cm^2$ per pulse. Typically, a single pulse will erode a depth in the range 0.1 to 1 micrometer of collagen from the cornea.

The shape of the add region (as well as ancillary PRK reprofiled regions) can be defined by irradiating the cornea through an aperture which may be of adjustable dimensions and shape and/or by using an optical stop which may also be adjustable in size and shape. To achieve a change in the refractive profile of the cornea of an eye, the object is irradiated by a pattern of light which varies with time so that different regions thereof receive different numbers of pulses and are, therefore, eroded to a different extent. Since the normal surface of a cornea is convex, the effect of a concave ablation profile effectively will be to flatten the surface of the cornea slightly. Flattening the surface of the cornea serves to decrease the refractive power of the eye. Conversely, increasing the curvature of the cornea (by effecting a convex erosion pattern), increases the refractive power of the eye.

If a circular iris is placed in the beam directed at the cornea of an eye and the iris is expanded (i.e., opened) while the pulses continue to be delivered, the central region of the cornea will, after a given period of time, have received more pulses (and will, consequently, have been eroded to a greater extent) than the surrounding peripheral regions.

Conversely, if a central stop of adjustable size is placed in the beam path and gradually expanded (e.g., like an umbrella opening slowly into the rain), the peripheral region will, after a period of time, have received more pulses (and, consequently, will have been eroded to a greater extent) than the central region. Thus, by controlling the number of pulses emitted for each setting of the aperture or central stop, the actual profile of the eroded surface of the cornea can be very closely controlled.

Alternatively, a collimated beam of laser energy can be transmitted through an optical system which causes the beam to have a region of divergence, a region of convergence, or both, before it is recollimated. A beam-shaping element is arranged to move along the beam axis in a region of convergence or divergence. The beam-shaping element may have an aperture or window to provide a variable size shaped beam. Alternatively, it may have a shaped stop portion where the beam is to be provided with a region of reduced or zero illumination of variable size. Combinations of apertures and stop portions may be provided if a more complex beam shape is required.

For convenience, the following description is in terms of a beam-shaping stop, but other types of stops will function in an analogous manner.

As such, a stop is moved along the axis of the beam, the beam diameter at the position of the stop will vary. Thus, when the stop is at one end of its range of travel (where the beam diameter is smallest), all (or a relatively large portion) of the beam will be passed, whereas when the stop is at the other end of its range of travel (maximum beam diameter), only a relatively small portion of the beam will pass the stop.

Only that portion of beam which passes the stop is recollimated and, thus, moving the stop axially along the beam will vary the size of the collimated output beam. The shape of the collimated output beam will be governed by the shape of the stop. Since the portion of the laser beam passing the stop is unaffected by it, the stop has no effect on the energy density of the beam but merely on its size.

Alternatively, the input beam may be uncollimated, in which case the optical elements of the system will have slightly different powers so as to ensure that the output beam is substantially collimated.

Since the shape of the beam delivered to the surface will correspond to the shape of the stop, a wide range of beam shapes is available.

Another approach to increasing the curvature of a cornea to provide an add region (or correct hyperopia, generally) can employ a concave lens, or other beam-shaping device, to create an annular region of illumination with a central region having zero or minimal illumination. By using a complementary convex conical lens in combination with a concave conical lens, the diameter of the illuminated annulus can be adjusted by altering the axial distance between the convex conical lens and the concave conical lens.

Alternatively, mirrors may be used. A mirror having an elliptical aperture may be located at 45 degrees to the illumination axis of the laser and positioned relative to the corneal surface which is to be irradiated, so that the image of the hole in the centre of the mirror is coincident with the centre of the region of the surface which is to be exposed. The size of the illuminated annulus can be altered by changing the mirror. A mirror is especially useful for providing a variable width non-illuminated strip. Two mirror portions may be provided separated by a gap which results in the non-illuminated strip. By moving the mirror portions towards and away from each other, the width of the strip can be varied.

The system described above, using a stop movable along the axis of the beam, may also be used to provided a beam with a central non-illuminated strip or spot. This is accomplished by providing a shaped central stop portion, either alone or in a aperture in a larger stop.

Where differential erosion is to be effected parallel to a line rather than around a point, cylindrical lenses or plain mirrors or slits may be used to produce rectangular or otherwise assymetric erosion profiles. Such techniques can be employed on a cornea to correct astigmatism and the like.

The various beam-shaping elements discussed above are described in more detail in the above-referenced U.S. Pat. No. 4,941,093, again herein incorporated by reference.

In one clinical procedure, for example, a laser system capable of measurement and reprofiling to create an add region for correction of presbyopia includes one of the above-described laser sources and beam-shaping means, as well as a control unit, a measurement and/or feedback means, and a suction cup for stabilizing the eyeball relative to the beam path. A surgical microscope can be employed to allow the surgeon to aim the laser correctly. After initial setting up and alignment using the microscope and measurement means, reprofiling is effected by appropriate operative signals from the control unit, with re-measurement between either each reprofiling step or after a sequence of steps in order to check progress towards the intended final profile of the cornea, including one or more add regions.

The wavelength of a laser used for corneal reprofiling is important. Typically the wavelength may be about 193 nm, although both shorter wavelengths down to 157 nm (for a Fluorine laser) and longer wavelengths up to 300 nm may be suitable for particular applications. Higher wavelengths are not preferred insofar as they are dangerous to the underlying structures of the eye. It is important that the laser energy should not penetrate substantially into the stroma because the cells lying below the collagen sublayers are easily damaged.

Since reprofiling requires use of a laser beam of changing, cross-sectional area, it is preferred to supply the energy through a UV optical system which produces a beam having constant energy per unit area regardless of its varying cross-sectional size. A suitable UV optical system for this purpose is an optical stop with first and second zoom systems upstream and downstream thereof, the zoom systems being coupled for simultaneous adjustment. Alternatively, the system described above using a movable apertured stop may be used or an adjustable iris.

Alternatively, the beam-shaping means of the present invention can comprise a masking means disposed between the laser means and the corneal surface for providing a predefined profile of resistance to erosion by laser radiation, such that, upon irradiation of the masking means, a portion of the laser radiation is selectively absorbed and another portion is transmitted to the surface in accordance with the mask profile to selectively erode the surface.

The masking means can further comprise a rigid structure which is affixed to the surface, in particular to the sclera of an eye, and a masking lens connected to the support structure and disposed above the cornea. The mask can be directly integrated with the support structure or, preferably, a transparent stage can be formed as part of the support structure to support and position the masking lens.

The masking means of the present invention provides a predefined profile of resistance (e.g., by erosion or photoabsorption) to laser radiation. Such profiles can be provided by varying the thickness or composition of the mask material. To provide the add region necessary to accommodate close viewing of objects in at least a portion of the optical zone, the mask should provide at least one region in which the corneal curvature is steeper.

When the thickness of the mask is varied, an add region can be provided, for example, by a convex or plano-convex shaped mask or by a mask which is aspheric or torroidal on at least one surface. Alternatively, the composition of the mask can be varied, for example, by incorporating more photoabsorptive elements into the portion of the mask which is aligned with the center of the desired add region. To correct refractive errors, as well as accommodate for presbyopia, composite masks of more complex but readily ascertainable shapes can be employed, or two or more separate masks can be used simultaneously or sequentially.

When erodable masks are employed, the mask material preferably has similar ablation characteristics to the cornea. Various polymeric materials can be employed as erodable masks, including, for example, poly(methyl methacrylate), poly(methyl styrene) and mixtures thereof. The ablation characters will be govern by the absorption coefficients. For corneal repro filing, the absorption coefficient of the masking material can range from about $10^4$ to about $10^5$ cm$^{-1}$. Preferably, the masking material has an absorption characteristic of micron or submicron etch depths per pulse similar to those of the cornea when it is exposed pulsed UV excimer laser radiation.

It should also be clear that the masking and other beam-shaping operations, such as a movable stop or aperture, or an adjustable iris can be used in conjunction with each other to achieve both a new overall curvature for the corneal surface (e.g., with an adjustable iris) and to create an add region within the new curvature (e.g., with an erodable mask).

According to another aspect of the invention, there is provided a method of reprofiling a surface comprising (a) locating a laser means relative to an optical axis of a surface, the laser means being operable to deliver laser radiation to the surface; and (b) disposing a masking means between the laser means and the surface, the masking means having a predefined profile of resistance to laser radiation, such that upon irradiation a portion of the radiation is selectively absorbed and another portion is transmitted to the surface in accordance with the mask profile to selectively erode the surface and thereby create at least one region in the cornea having a different focal point in order to assist the eye in accommodating for close-viewing conditions.

The invention will next be described in connection with certain illustrated embodiments; however, it should be clear that those skilled in the art can make various modifications, additions and subtractions without departing from the spirit or scope of the invention. For example, the invention can be used in connection with corneal transplants where a donor button is inserted into the patient's eye. As part of such a procedure, the transplanted cornea can be repro filed to provide an add region which facilitates close viewing of objects.

BRIEF DESCRIPTION OF THE DRAWINGS

The invention will now be described by way of example with reference to the accompanying drawings, in which.

DETAILED DESCRIPTION

Figure 1:
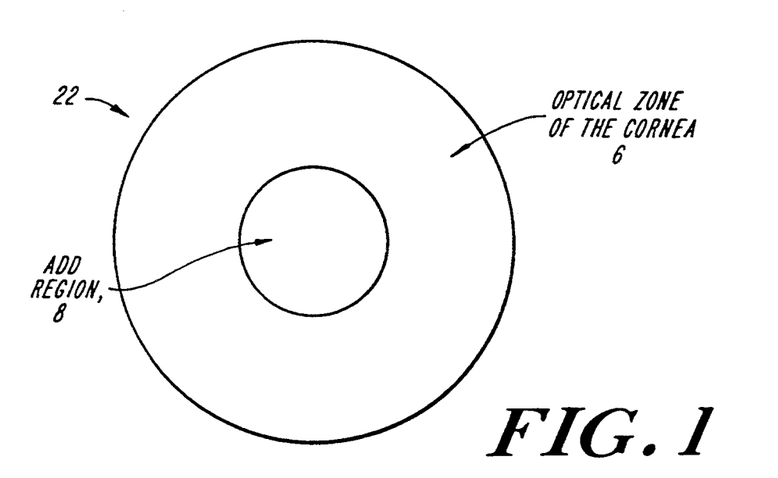
FIG. 1 is a schematic front (anterior) view of a cornea showing one embodiment of an add region constructed according to the invention to compensate for presbyopia.
Figure 2:
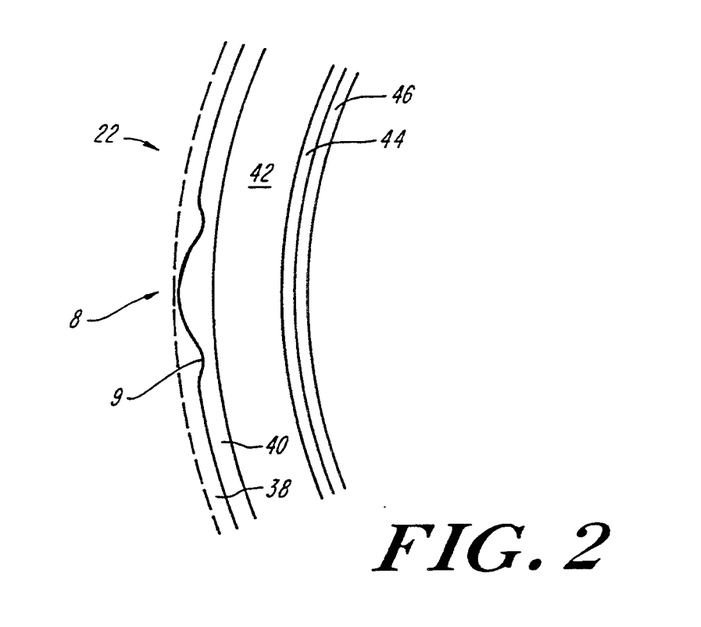
FIG. 2 is a schematic cross-sectional illustration of the corneal tissue showing the layers of the cornea and the formation of an add region according to the invention.

FIGS. 1 and 2 illustrate a simple procedure according to the present invention in which an add region 8 is created within the optical zone 6 of the cornea 22. As shown in the front view of FIG. 1, the add region 8 can be situated below the optical center of the cornea 22 in a manner akin to the location of an "add" lens in bifocal glasses.

As shown in more detail in FIG. 2, the cornea is a thin shell with nearly concentric surfaces with a central thickness of about 520 microns, an index of refraction of about 1.377, and a nominal radius of curvature of about 7.86 millimeters. The outer layer, the epithelium 38, is about 50 microns thick. The epithelial cells are capable of very rapid regrowth. The innermost layer consists of a single layer of endothelial cells 46, which do reproduce.

The central bulk of the cornea is the stroma 42, which consists primarily of collagen fibers arranged in interlocking, shell-like layers. Type I, II, V, and VI collagen have been identified as the major components of the human stroma. Bowman's membrane 40, which forms the outer elastic lamina, is a rigid fibrillar structure not tending to cut or fracture, while Descemet's membrane 46, which forms the inner elastic lamina, is very brittle but elastic and has a tendency to curl. Together, the Bowman's and Descemet's membranes 42, 46 define the necessary curvature to the stroma tissue 42.

The collagen of the stroma 42 is arranged in a regular pattern of lamellae, while the collagen of Bowman's layer 40 does not have organized collagen arrays. Bowman's membrane 40 is typically about 20-30 microns thick and differs from the stroma in that it is acellular and contains mainly type V collagen. The present invention is directed in one aspect to systems and methods for selectively repro filing regions of Bowman's membrane 40 without substantial penetration into the stroma 42. It has been discovered that Bowman's membrane 40 or the stroma proper 42 can be readily and easily repro filed by photoablation to provide an add region 8 and a blend zone 9, and thereby compensate for presbyopia.

The procedure illustrated in FIGS. 1 and 2 essentially creates a region 8 of steeper curvature to a corneal surface which would otherwise be unable to accommodate the focusing of near objects. However, it should be clear that the add region 8 could also be formed by preserving the original curvature of a myopic eye within a particular region and ablating the remainder of the optically zone 6 to impart a flattened curvature that would accommodate the viewing of more distant objects. In either case, the net result would be the same, with the cornea having a least two distinct curvatures, one of which is suitable to viewing near objects.

In practice, the overlying epithelium 38 of the cornea 22 typically is removed prior to repro filing and may, for example, be ablated by the initial pulses of a laser, whereafter the laser can erode the exposed Bowman's membrane 40 or the stroma 42 to effect a permanent change of curvature within the add region, the overlying epithelium re-forming by the natural healing process, after erosion. In one preferred embodiment, the operation is performed so as to avoid substantial penetration into the stroma 42, so as to minimize the disturbance of the fibrillar regularity of the cornea proper and, thereby, reduce the trauma and risk of the procedure. Alternatively, in some applications, it may be preferable to penetrate into the stroma in order to ensure a properly shaped bifocal or multifocal configuration of the corneal surface.

Figure 3:
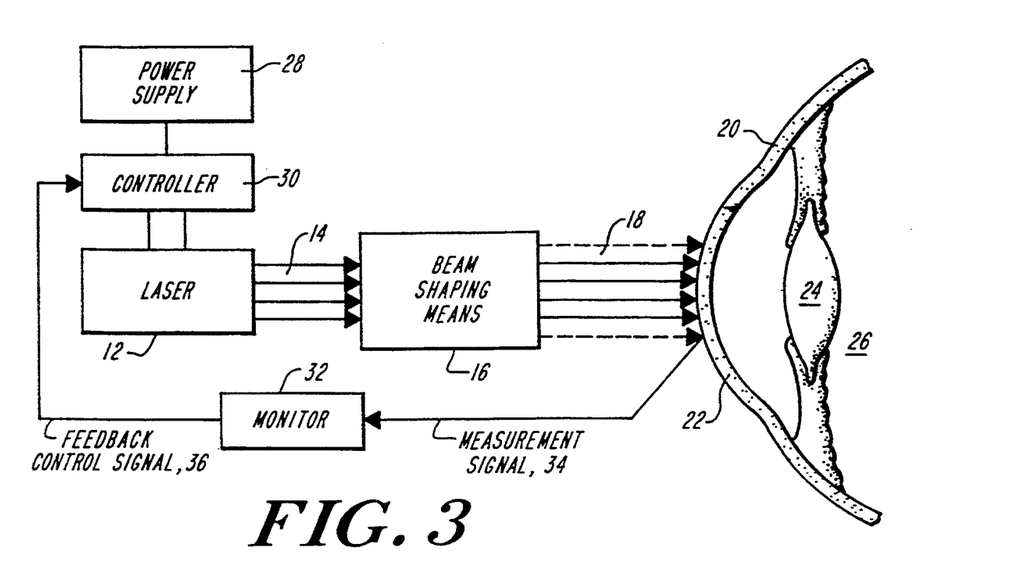
FIG. 3 is a diagrammatic illustration of an apparatus for practicing a method of reprofiling the surface of a cornea to provide at least one region having a different focal length, in accordance with the invention.

In FIG. 3, a laser system 10 for correcting presbyopia is shown, including a laser 12 which provides a radiation output 14 to a beam-shaping element 16, which, in turn, imposes a defined ablation profile onto the surface of an eye 20. As shown, the eye 20 includes a cornea 22, lens 24 and the vitreous body 26, which together define an optical path for vision. A portion of the laser radiation 18 is selectively transmitted by the beam-shaping means 16 and irradiates the surface of the cornea 22 to effect repro filing, in accordance with the present invention.

The laser 12 can be powered by a power supply unit 28 and controlled by controller 30 which can be adjustable to cause the laser to produce pulses of light at a specific frequency and/or intensity. To further control the laser 12, a monitor 32 can be provided which receives measurement signals 34 from the beam-shaping means 16 and/or the cornea 22 while it is exposed to irradiation by the laser 12. The monitor 32 generates a feedback control signal which is communicated to the controller 30 for controlling the laser 12 and/or optionally for controlling the beam-shaping means in some embodiments.

Figure 4:
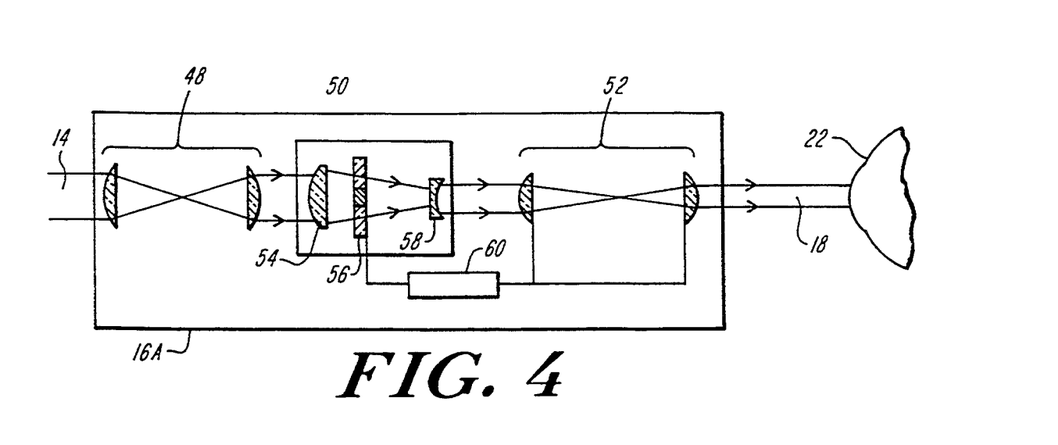
FIG. 4 is a diagrammatic illustration of one embodiment of a beam-shaping optical assembly for use in the apparatus of FIG. 3.

In FIG. 4, an embodiment of a beam-shaping means 16A is shown for use in a system, such as that described above in connection with FIG. 3. In this embodiment, laser light 14 (which is preferably collimated and of substantially uniform cross-sectional intensity) passes through the optical elements of the beam-shaping means 16A to create an output beam 18 of desired shape and size. Output beam 18 is delivered to the surface of the cornea 22.

The beam-shaping element 16A of FIG. 4 includes a first relay telescope 48 which delivers the beam to a dimension control means 50. The dimensional control means 50 can include, for example, a planoconvex lens 54 and a planoconcave lens 58, which cooperate to define a converging (or, alternatively, a diverging) beam portion between them.

A stop 56 (e.g., a transmissive element having a central opaque region) is movable along the beam axis over the converging beam portion. In order to vary the size of the ring-shaped exposure area on the cornea, the stop 56 is moved axially along the beam between the lens 54, 58. When the stop 56 is adjacent the plano-concave lens 54, the plane of the stop intersects the converging beam at its smallest diameter. Thus, a relatively small annular portion of the beam passes through the stop 56 as the remainder strikes the stop and is absorbed or deflected. However, if the stop 56 is moved so as to be adjacent to the planoconvex lens 54, the plane of the stop intersects the converging beam portion at its greatest diameter. In this position, a relatively large portion of the laser beam passes through the aperture in the stop 56. In either position, the central position of the beam is not passed through the aperture, and it should be evident that so long as the input beam 14 is collimated and substantially uniform in its cross-sectional intensity, the stop 56 will not affect the energy density of the transmitted beam regardless of the thickness of the annulus projected or imaged onto the eye.

From the beam-shaping means 50, a second relay telescope 52 delivers the output beam 18 to the cornea 22. Since the stop 56 is moved axially along the beam to vary the size of the illuminated area on the surface of the cornea 56, the second relay telescope 52 will not always provide a precisely focused image of the aperture in the stop 56, if the telescope 52 has a fixed focal length. Accordingly, a gearing arrangement 60 can be provided to synchronize the movement of the stop 56 with corresponding movement of the elements of the second relay telescope to maintain an in-focus image on the cornea 22.

Figure 5A:
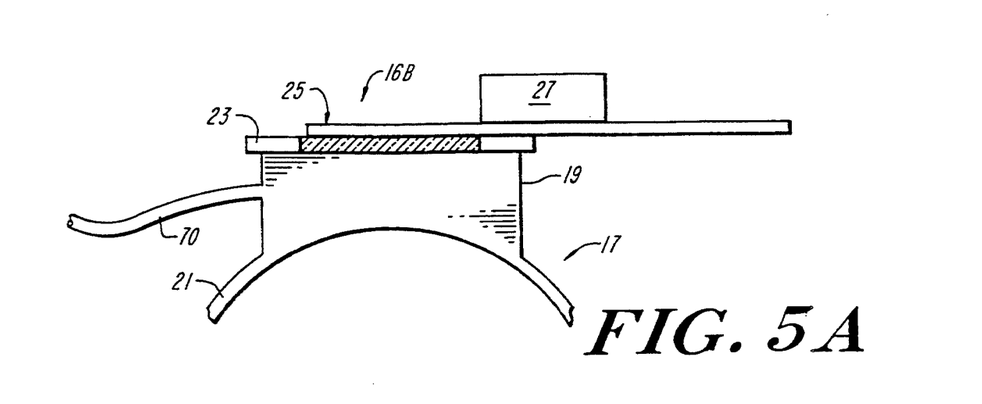
FIG. 5A is a schematic side view of another embodiment of a beam-shaping optical assembly for use in the apparatus of FIG. 3.
Figure 5B:
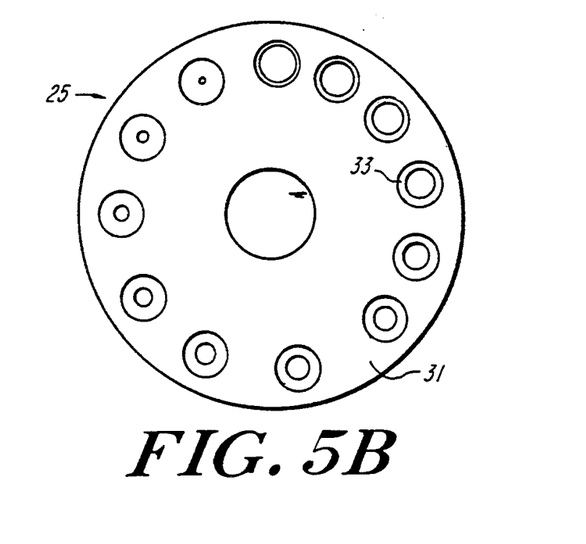
FIG. 5B is a schematic top view of the aperture wheel of the beam-shaping assembly shown in FIG. 5A.

In FIGS. 5A and 5B, an alternative beam shaping means 16B is shown for use in the system 10 of FIG. 3. As illustrated, the beam-shaping means 16B comprises an eyecup 17 having a surface 21 adapted to rest upon the eye, a vertical sidewall 19 and a horizontal surface 23 with at least a portion of surface 23, preferably being transmissive to laser radiation. Disposed upon or above the horizontal surface 23 is an aperture wheel 25, which is preferably driven by motor 27.

The entire structure 16B can be placed upon the sclera of an eye, leaving the corneal surface unobstructed. A flexible tube 70 supplies vacuum suction to the cup, so as to clamp it to the eye with a force sufficient to hold it in place but not distort the shape of the cornea.

FIG. 5B shows a top view of aperture wheel 25, including plate 31 and a plurality of stops 33, each of which defines a annular transmissive region of different size.

Figure 6A:
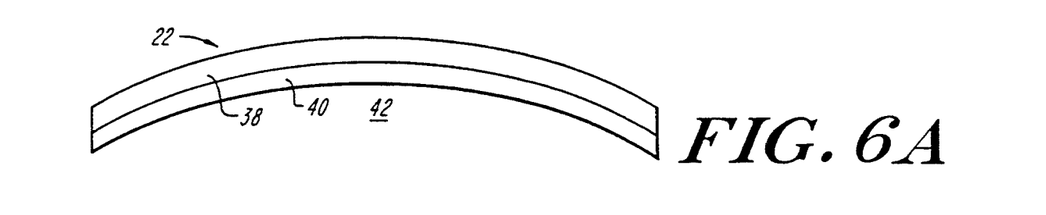
FIGS. 6A-6D are schematic illustrations of how a beam-shaping assembly can operate to increase the curvature of the cornea within a selected add region by selective ablation of tissue from Bowman's membrane.
Figure 6B:
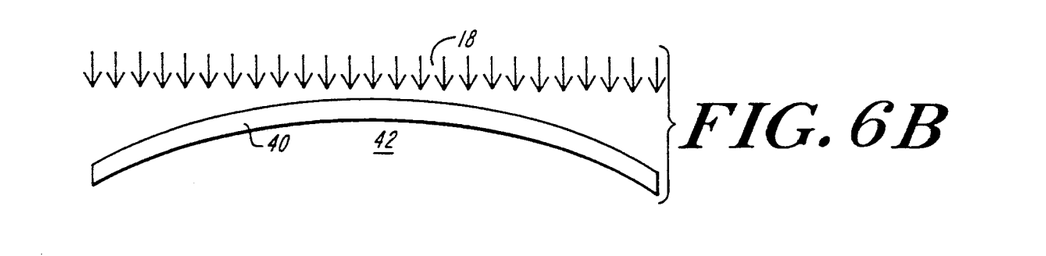

FIGS. 6A-6D are schematic illustrations of how the beam-shaping means of FIG. 3 can operate to create an add region in a selected portion of the cornea 22 by increasing the curvature of the cornea in the region. In FIG. 6A, the intact surface layers of the cornea 22 are shown comprising the epithelium 38, Bowman's membrane 40 and the upper portion of the stroma 42. In FIG. 6B, a large aperture is employed to ablate all (or a substantial portion) of the epithelial layer 38 of the cornea 22 in the selected add region of the optical zone and so as expose the surface of Bowman's membrane 40.

Figure 6C:
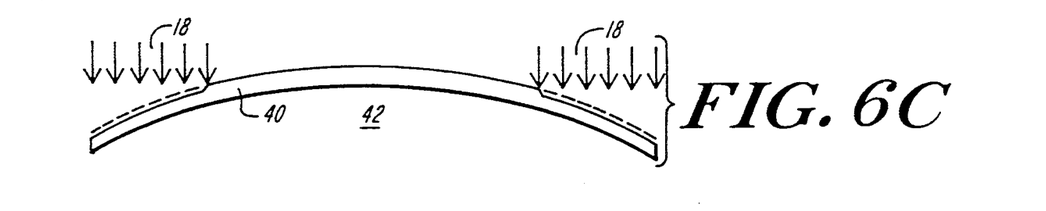
Figure 6D:
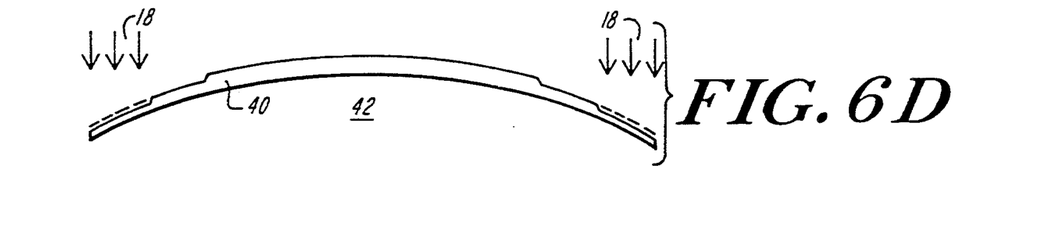

A first annular ablation region of wide cross-sectional area is then created in Bowman's membrane 40, as shown in FIG. 6C. A narrower ring of further ablation is then created, as shown in FIG. 6D, to create a steepened curvature. Thus, a stop having a central beam-stopping region is employed to create a ring-like ablation zone which is shifted to the periphery of the optical zone so as to create a "hill-like" profile of ablation, thereby steepening the curvature of the cornea upon regrowth of the epithelial layer over the resculpted Bowman's membrane surface.

It should be clear that the actual procedure would be carried out with a substantially greater number of steps to achieve a smooth curve and minimize the step-effects, and in some cases, it may be desirable to penetrate into the upper portions of the stroma. Additionally, the order of the steps can be reversed, e.g., by starting with a very narrow peripheral ablation ring and then gradually increasing the thickness of the annular beam. Upon completion of the laser surgery, the epithelium regrows with a uniform thickness and produces a new corneal curvature determined by the new curvature of the remaining Bowman's membrane tissue.

Figure 7A:
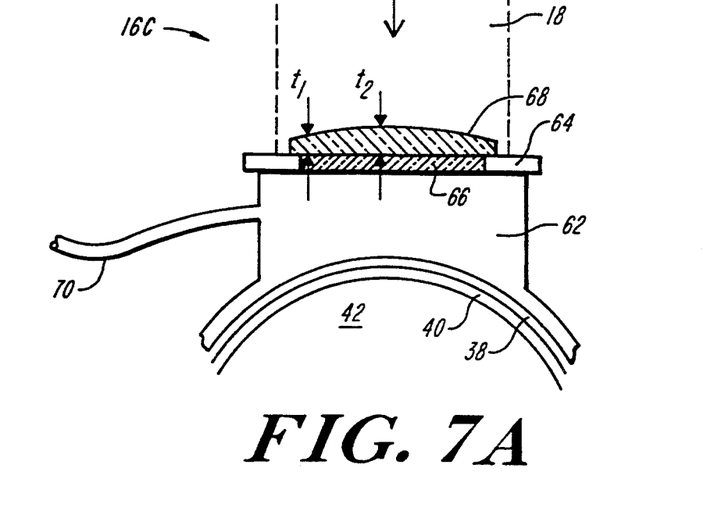
FIGS. 7A-7B are diagrammatic illustrations of another embodiment of a beam-shaping element employing a laser radiation absorptive mask for use in the apparatus of FIG. 3.
Figure 7B:
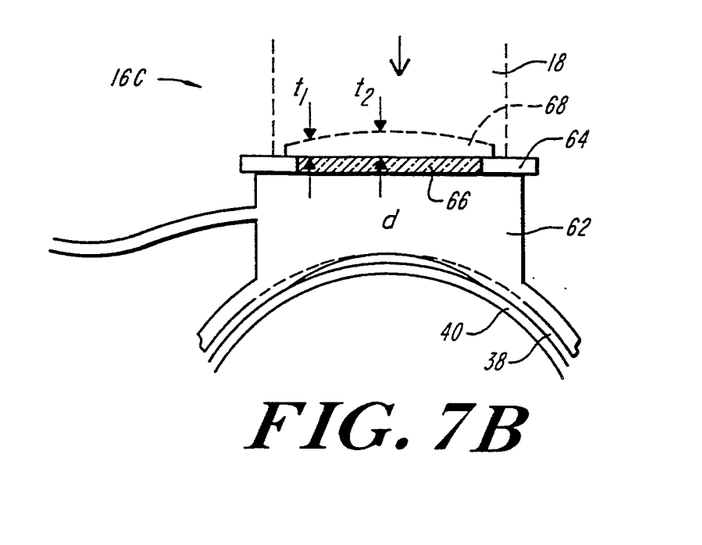

In FIGS. 7A and 7B, yet another alternative embodiment of the beam-shaping means 16 of FIG. 3 is shown in more detail. As illustrated, the beam-shaping means 16C comprises a mask system, including a suction cup 62 which provides a support structure having substantial rigid walls and a horizontal surface 64. At least a portion of the horizontal surface 64 is formed as a transparent stage 66. Preferably, the remainder of surface 64 is opaque to laser radiation. Disposed upon the transparent stage 66 is a mask or masking lens 68.

The entire structure can be placed upon the sclera of an eye, leaving the corneal surface unobstructed. A flexible tube 70 supplies vacuum suction to the cup, so as to clamp it to the eye with a force sufficient to hold it in place but not distort the shape of the cornea.

The mask system 16C can be rigidly connected to the laser or otherwise optically aligned therewith, such that radiation from the laser can be selectively transmitted through the mask 68 to produce the desired erosion of the surface by pulses of laser energy.

The selected lens material can be any material which creates a profile of resistance to the ablative laser radiation, including, for example, graded intensity materials, photobleachable materials or photodecomposable materials. In one preferred embodiment, the mask 68 is a material which is erodable by laser radiation and preferably has ablation characteristics substantially identical to the cornea. For example, the erodable masks of the present invention can be formed from plastic material, such as poly(methyl methacrylate) (PMMA) or poly(methyl styrene) (P S). These polymers are both biocompatible and can be efficiently eroded by laser radiation, i.e., by a pulsed ArF excimer laser (193 nm). These polymers are mutually soluble in each other, and by changing the concentration of PS in PMMA, absorption coefficients can be varied from about $10^4$ to about $10^5$ cm$^{-1}$. Other organic polymers exhibiting suitable ablation characteristics can also be employed in the manufacture of erodable masks.

Preferably, the polymeric material has an absorption characteristic of micron or submicron etch depths per pulse similar to those of the cornea. For further details on organic polymers suitable for construction of masks, see Cole et al., "Dependence of Photo-etching Rates of Polymers at 193 nm on Optical Absorption Coefficients," Vol. 48, *Applied Physics letters*, pp. 76-77 (1986), herein incorporated by reference.

Various techniques can be employed to manufacture the lenses used in the present invention from PMMA or PS. These techniques included injection molding, casting, machining and spin casting. Manufacture by laser machining can also be employed. In one typical technique, a solution of PMMA or PS is prepared in toluene and spin cast in a suitably-shaped cup to obtain a smooth, uniform lens having a pre-defined profile thickness. Depending upon the concentration of PS in PMMA, a suitable absorption coefficient is obtained. The films can then be removed from the spin cup and vacuumed baked to residual solvent.

Alternatively, the erodable mask can be made of a material having a variable composition, such that pre-defined regions of the mask selectively absorb greater amounts of laser radiation, even though the entire mask has a uniform thickness. Again, materials, such as PMMA and PS, can be employed in varying concentrations in the erodable mask to achieve the variable composition of the mask.

FIG. 7B illustrates the principle involved in eroding a surface to effect repro filing thereof, in accordance with the present invention. Although the transparent stage shown in the figures is substantially horizontal, it should be clear that it can also take other shapes (e.g., concave or convex spherical forms) and can further include a cup-shaped rim to support a liquid or semiliquid masking lens.

In FIGS. 7A and 7B, the surface layers of the cornea are again shown, including the epithelium 38, Bowman's membrane 40, and the upper portion of the stroma 42. Reference 68 denotes a masking lens disposed over the area of the cornea to be treated. The lens 68 is uniformly irradiated with a beam of radiation 18 obtained from a pulsed UV laser source.

During the irradiation, the lens 68 is gradually ablated, and an increasing area of the cornea becomes exposed to erosion. At the moment when the lens 68 has been wholly ablated, the surface of the cornea has been eroded as indicated, to the extent necessary to complete reprofiling over the area of the lens. As shown in FIGS. 7A-7B, the maximum thickness $t_1$ of the lens 68 exceeds the minimum thickness $t_2$ by an amount equal to the maximum depth (d) of the corneal erosion desired. By controlling the shape, thickness and/or composition of the lens 68, photoablation of the cornea can be precisely confined to the epithelium 38 and Bowman's membrane 40 or the upper stromal region 42 of the cornea. Together, FIGS. 7A and 7B illustrate the formation of an add region of steepened curvature in the cornea.

Figure 8A:
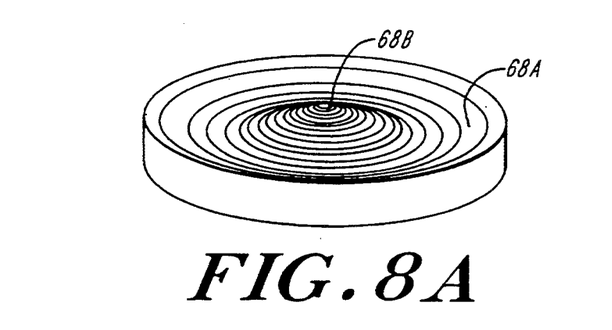
FIGS. 8A and 8B and 8C are schematic perspective and side views, respectively, of another photoabsorptive mask for use as a beam-shaping element in the performance of composite procedure to correct myopia and at the same time provide an add region to compensate for presbyopia.
Figure 8B:
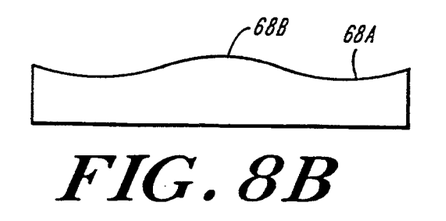
Figure 8C:
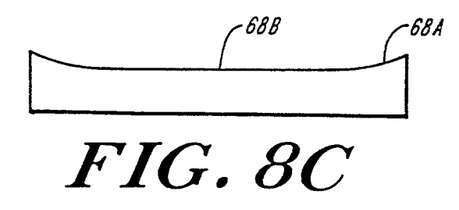

In FIGS. 8A-8C, composite masks for use in connection with the beam-shaping means 16C of FIG. 7a are shown in order to simultaneously correct myopic conditions and provide an add region for presbyopia. In use, the composite mask is disposed in the path of ablative radiation and aligned with the corneal surface. The curvature of the major portion 68A of the mask is chosen to provide an overall flattening of the cornea and, thereby, compensate for nearsightedness, while portion 68B is selected to provide localized steepening of the corneal surface to accommodate the viewing of close objects. As shown in FIG. 8C, the curvature of portion 68B can, in fact, be flat when the natural myopic shape of the central region matches that of the desired "add region". In such a case, the natural curvature would be preserved within the add region and modified only in peripheral portion of the optical zone.

Similar results can be obtained by using an adjustable iris to flatten a myopic corneal curvature along a portion (e.g., the periphery) of the cornea while preserving the steeper curvature (e.g., as an "add region") in a central portion of the cornea.

Figures 9A, 9B:
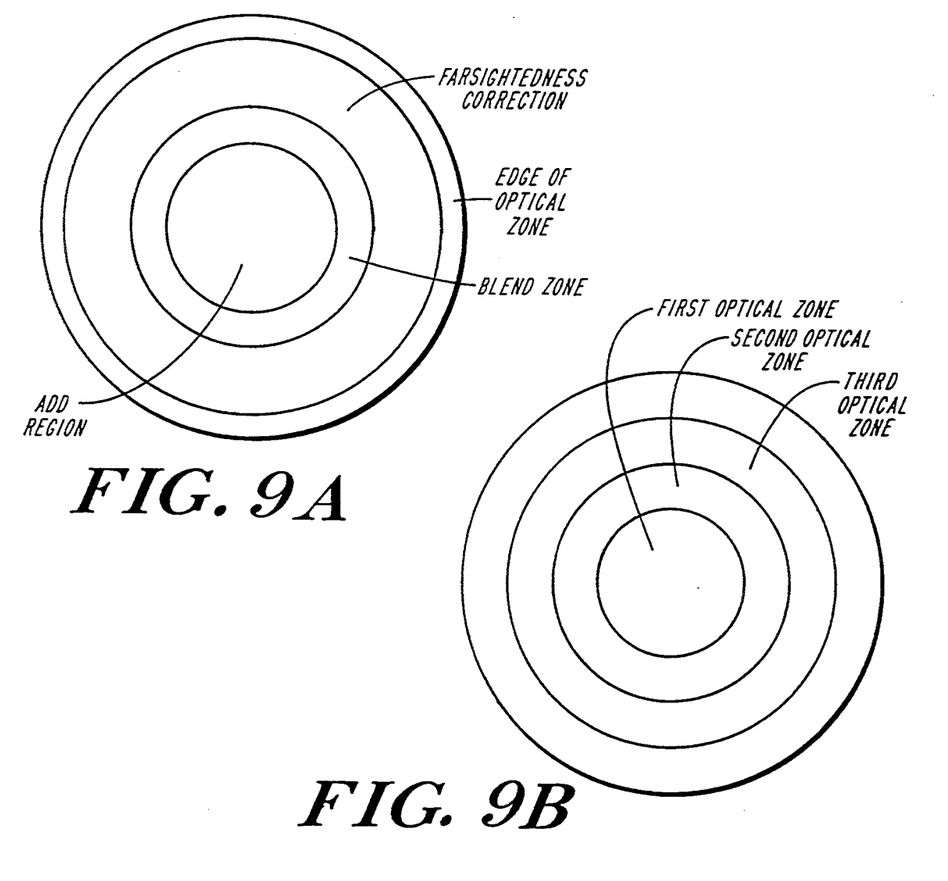
FIGS. 9A-9B are schematic illustrations of alternative configurations of add regions which can be created on the surface of the cornea in accordance with the invention.

FIGS. 9A and 9B illustrate alternative designs for add regions. In FIG. 9A, a design is shown for correcting hyperopia over the major portion of the cornea's optical zone and a second, yet steeper curvature is created to compensate for presbyopia. (In this embodiment, as well as others, it may be preferable to create a "blend zone" as shown, in order to avoid sharp discontinuities in the corneal surface curvature.) Finally, as shown in FIG. 9B, it may be desirable to provide multifocal regions with each region providing a different depth of focus.

Figure 10:
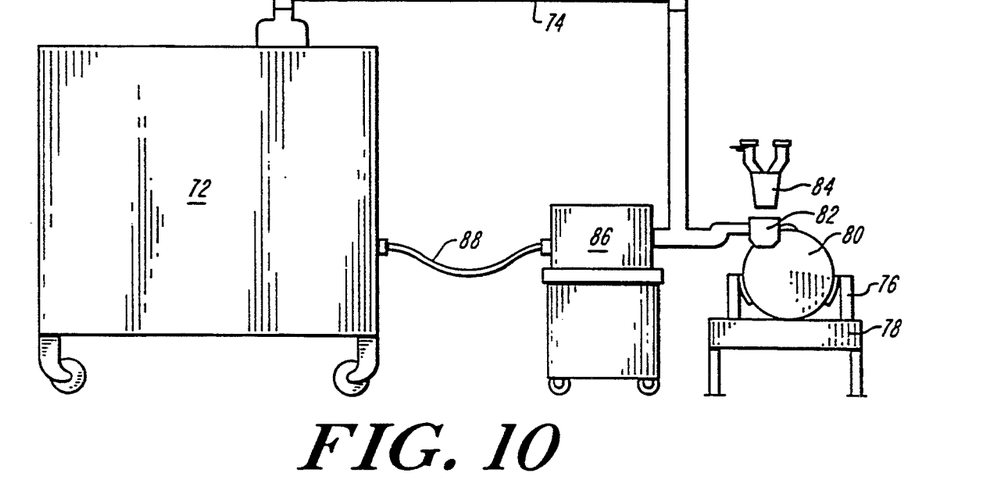
FIG. 10 is an overall schematic view of a clinical system for measurement and reprofiling operations during laser corneal surgery.

FIG. 10 illustrates an apparatus for performing a method of the present invention for repro filing the cornea of a human eye. A laser and associated control circuitry is contained in a housing 72. The beam-forming optics, for providing a beam of desired shape and size, can also be contained within the housing 72 together with the laser power supply control circuits. An optical wave guide 74, which can be flexible or rigid and includes suitable mirrors, prisms and lenses, is provided to transmit the laser beam output from the housing 72 to the patient 80. The patient 80 is lying face-upwards on an operating table 78. The operating table 78 will support the patient's head against vertical movement. If desired, side supports 76 may also be provided to restrain sideways movement of the patient's head.

When a light restrictive mask system of the present invention (as described above in connection with FIGS. 5A-5B or FIGS. 7A-7B) is employed, it can be disposed within an eyepiece 82 adapted to fit over the patient's eye. (Alternatively, when the beam-stopping optics of FIG. 4 are employed, they can be integrated into the waveguide 74.) The eyepiece 58 can include suction means for providing suction to clamp the eyepiece over the patient's eye. The eyepiece can include a cup of resiliently-deformed, flexible material such as rubber or plastic, which, when placed over the eyeball, will clamp thereto upon being evacuated. Alternately the eyepiece can be secured mechanically to sclera (e.g., with a so-called Thornton ring). Also disposed within the eyepiece are suitable optical elements for transmitting the laser radiation to the surface of the eye. The masking system or the beam-stopping optics as described above are preset based on measurements of the patient's eye and designed to impart the desired refraction correction upon use.

During the operation, the eye can be observed using a surgical microscope 84 which is supported above the patient by any convenient means. The surgical microscope 84 may be connected to the eyepiece 82 but will more normally be separated therefrom and supported by an arm (not shown) from the ceiling or by a cantilever (not shown).

A measuring device 86 can also be employed in conjunction with the present apparatus to measure the changes in the curvature of the cornea following operation. Such a measuring device 86 can also be employed to monitor the degree of erosion of the erodable lens when used during treatment. The measuring device can take the form of a commercially-available keratometer or other suitable device and can be connected, as shown in FIG. 10, directly to the laser optical path or may be movable when needed to occupy the position shown for the surgical microscope 84, the operator moving the measuring device 86 or the microscope 84 into position, as required.

The measuring device 86 can further provide the feedback control, as shown in FIG. 3, whereby information from optical or other inspection of the surface which is being exposed to laser erosion is used to control the actual duration and amplitude of the pulses supplied by the laser and may be tuned so as to produce just the desire degree of erosion of the surface by each pulse.

Figure 11:
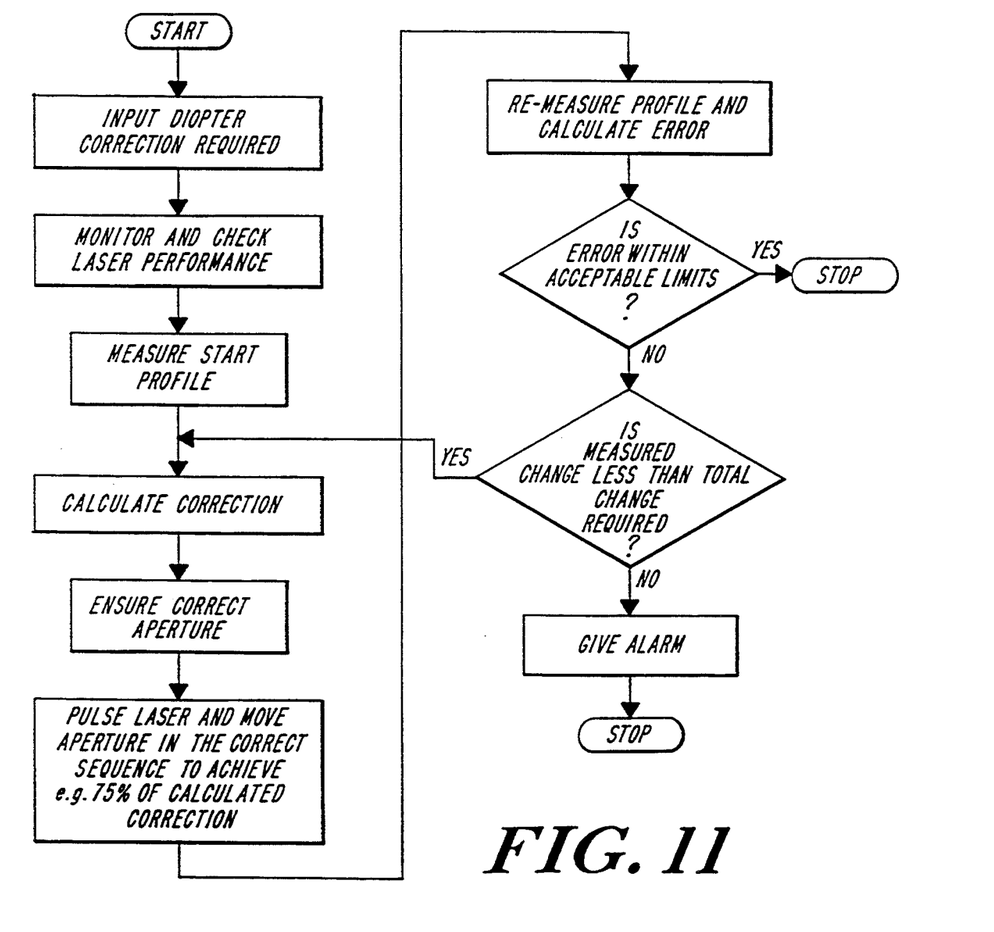
FIG. 11 is a flow diagram illustrating a method of feedback control, in accordance with the invention.

In FIG. 11, a flow diagram is shown of the controller 30 during feedback control operation (particularly, in connection with the beam-shaping optics of FIG. 4 or FIGS. 5A-5B). The controller is preferably provided at least in part by a microprocessor or microcomputer which has been programmed with the appropriate diopter (or more complex shape) change desired. In this method, a commercially-available keratometer can be used first to check that suction cup of eyepiece 82 has not affected the corneal profile. Then the beam dimension control is operated to impart a desired change in the profile of the corneal surface and thereby provide one or more add regions.

The parameters can be selected to produce 75 percent of the desired final correction to the corneal surface, particularly within the tissue of Bowman's membrane or the upper regions of the stroma. The cornea is then measured again using the keratometer and the exact correction remaining to be made is determined. The laser apparatus is then operated again in a similar manner to that just described, with the parameters selected to produce 75 percent of the correction remaining to be made. The process is then repeated until the correction remaining to be made is considered to lie within acceptable limits.

What is claimed is:

1. A method of reprofiling a cornea of an eye, the cornea having an initial curvature, to provide the eye with a multi-focal capability to compensate for presbyopia, the method comprising:
   aligning a laser means with the cornea, the laser means being operable to deliver ablative laser radiation to the cornea; and
   selectively exposing the cornea to said ablative radiation such that an add region of different curvature and a second, distinct focal point is created in a portion of the cornea.

2. The method of claim 1 wherein the step of selectively exposing the cornea further includes disposing a mask means between the laser means and the cornea, the masking means having a pre-defined profile of resistance to erosion by laser radiation, such that upon irradiation a portion of the radiation is selectively absorbed and another portion is transmitted to the surface in accordance with the mask profile to selectively erode the surface.

3. The method of claim 2 wherein the method further includes varying the thickness of the masking means to provide the profile of resistance.

4. The method of claim 2 wherein the method further includes varying the composition of the masking means to provide to the profile of resistance.

5. The method of claim 1 wherein the step of varying the exposure area further includes varying the exposure area by disposing a variable aperture means between the laser means and the cornea to vary the beam size and thereby provide selective ablation.

6. The method of claim 5 wherein the step of varying the exposure area further includes employing an optical system for receiving a laser beam provided by the laser means, the optical system providing at least one region of divergence or convergence of the beam and, further, including a beam-shaping stop means movable axially along the beam in the region of convergence or divergence, said stop means having at least one beam-shaping window and one beam-shaping stop portion, whereby the proportion of the total beam cross-section which passes through said window or strikes said stop portion varies with the movement of the stop means axially of the beam in that region.

7. A method according to claim 5 in which the size of the area to be eroded by the pulses is varied in a controlled manner during the step of operating the laser.

8. The method of claim 1 wherein the method of reprofiling further comprises:
   measuring a parameter which is a function of the shape of the cornea;
   comparing such measurement with a desired value; and
   deriving a feedback control signal from such comparison to provide further control for the laser means.

9. The method of claim 8 wherein the step of measuring a parameter further comprises measuring the curvature of the corneal surface.

10. The method of claim 8 wherein the step of measuring a parameter further comprises measuring the thickness of Bowman's membrane remaining after an initial operation of laser ablation.

* * * * *